United States Patent [19]

Marquis et al.

[11] 4,212,821
[45] Jul. 15, 1980

[54] PROCESS OF MAKING DIAMINODIPHENYLMETHANES

[75] Inventors: Edward T. Marquis; Walter H. Brader, Jr., both of Austin, Tex.

[73] Assignee: Texaco Development Corp., White Plains, N.Y.

[21] Appl. No.: 12,680

[22] Filed: Feb. 16, 1979

Related U.S. Application Data

[63] Continuation-in-part of Ser. No. 927,266, Jul. 21, 1978, abandoned.

[51] Int. Cl.² .............................................. C07C 85/18
[52] U.S. Cl. ........................... 260/570 D; 260/501.21
[58] Field of Search ..................................... 260/570 D

[56] References Cited

U.S. PATENT DOCUMENTS 3,297,759  1/1967  Curtiss et al. ......................... 260/570
3,478,099  11/1965  Ross et al. ............................ 260/570

FOREIGN PATENT DOCUMENTS 1229561  4/1971  United Kingdom .................... 260/570

Primary Examiner—Robert V. Hines
Attorney, Agent, or Firm—Carl G. Ries; Robert A. Kulason; James L. Bailey

[57] ABSTRACT

Covers a method of preparing diaminodiphenylmethanes and higher homologues thereof which comprises the step of condensing aniline and formaldehyde in the presence of hydroxy ethane sulfonic acid catalyst.

3 Claims, No Drawings

PROCESS OF MAKING DIAMINODIPHENYLMETHANES

REFERENCE TO RELATED DISCLOSURE

This application is a continuation-in-part application of Serial No. 927,266, filed July 21, 1978 and now abandoned.

BACKGROUND OF THE INVENTION

1. Field of the Invention

This invention relates to the field of polyamines.

2. Description of the Prior Art

The process of producing aromatic polyamines by the reaction of aniline and formaldehyde is well known and described for example in U.S. Pat. Nos. 2,683,730; 3,277,173; 3,344,162; and 3,362,979. By phosgenating these amines the corresponding isocyanates are obtained. The polyamines produced by the condensation of aniline and formaldehyde usually consist of a mixture of poly(methylenephenylamines) of functionality greater than two and the 2,2', 2,4' and 4,4' isomers of diamino-diphenylmethane. By reaction with phosgene a corresponding mixture of polyisocyanates and diisocyanates is prepared which is useful in producing, for example, polyurethane foam or is used as an epoxy curing agent.

One mode of reacting aniline with formaldehyde is to effect this reaction in the presence of a strong mineral acid, such as hydrochloric acid. Here a reaction occurs between the corresponding aniline hydrochloride and formaldehyde to provide a reaction mixture which, upon neutralization with a base, may be treated to recover the polyphenylamines. This process has left much to be desired. For example, it is necessary to utilize large quantities of both a mineral acid and a base which adversely affect the economics of the process and also the ease of conducting the reaction. In addition, the use of large quantities of mineral acids and the bases presents a severe corrosion problem. Also, the inorganic salt formed poses environmental difficulties with respect to disposal and/or recovery.

As an improvement to the conventional mineral acid catalyzed aniline-formaldehyde condensation, use of a solid acidic siliceous catalyst has been proposed (see U.S. Pat. No. 3,362,979). This is economically favorable over the conventional hydrochloric acid catalyzed process, since use of large quantities of corrosive acid and caustic are avoided. However, even this process has some drawbacks, particularly, in that the rate of reaction is not as rapid as desired and rearrangement of product amines at conventional conditions is not considered sufficiently complete.

Another acid catalyst utilized in the above reaction is methane sulfonic acid. However, this acid as well as hydrochloric acid forms insoluble salts of aniline in the initial stage of the reaction creating a problem of solids build-up and fouling of reactor stirring equipment. Also, there exists a problem in that both excess hydrochloric acid and methane sulfonic acid remaining after reaction are difficult to recover by water extraction. Lastly, when used as a recycle catalyst, the amine salts of methane sulfonic acid are usually solids at room temperature when the recycle catalyst is concentrated causing handling difficulties.

SUMMARY OF THE INVENTION

The invention relates to a process for making aromatic polyamines by the reaction of aniline and formaldehyde in the presence of hydroxy ethane sulfonic acid catalyst.

DESCRIPTION OF THE PREFERRED EMBODIMENTS

A method of preparing diaminodiphenylmethane and higher homologues thereof has now been discovered. The invention comprises the step of condensing aniline and formaldehyde in the presence of hydroxy ethane sulfonic acid catalyst. A mixture of products is produced which includes the diaminodiphenylmethane isomers comprising the 2,2', 2,4', and 4,4' diamine isomers and higher homologues thereof or polymethylene polyphenylamines. The latter are higher molecular weight condensation polymers of the formaldehyde and the aniline and are considered homologues of the simple diaminodiphenylmethane isomers.

Depending upon reaction conditions, amount of catalyst employed, proportions of the reactants, and other variables, the proportions of diamines, and higher polyamines present in the final reaction mixture may be widely varied. However, usually the reaction mixture contains 20–80 percent by weight of diamine with the remainder being higher polyamines thereof. More often, the percentage of diamines in the mixture is 30–70 percent and most often ranges from about 35 to about 55 weight percent. Correspondingly, the polymeric products higher than the dimer products usually in the preferred embodiment range from 30 to 70 percent by weight, and most often range from about 45 to about 65 percent by weight. With respect to product distribution of the dimer usually 1–10 percent by weight of total dimer is the 2,2' isomer, with the remainder being 2,4' and 4,4' isomers. Most often the content of dimer is 1–5 percent 2,2' isomer with the remainder, 95–99 percent, being 2,4' and 4,4' isomers, based on total dimer content. Generally, the higher molecular weight polymethylene polyphenylpolyamines have an average functionality of from about 2.2 to about 4.5, more often 2.2–3.0.

Hydroxy ethane sulfonic acid is well-known and need little elaboration.

The amount of catalyst used here may be varied according to the choice of the experimenter. Usually, however, 10–70 mole percent catalyst based on moles of aniline is employed. More often, the amount of catalyst utilized is 20–40 mole percent based on moles of aniline.

In order to prepare the methylene-bridged polyphenyl polyamines (term includes both diaminodiphenylmethane isomers and higher homologues thereof or higher polymers) the following process conditions are preferred.

The molar ratio of aniline to formaldehyde may be varied within comparatively wide limits. Thus, for example, from about 1 to about 10 mols of aniline may be employed per mol of formaldehyde. In general, at the lower aniline:HCHO ratios, such as ratios of from about 1:1 to about 2.5:1, the higher polymers will be formed preferentially and the yield of higher polymers is in excess of the yield of dimer. However, as progressively larger amounts of aniline are used, the yield of dimer is progressively increased at the expense of polymer yield. Thus, with aniline to formadehyde ratios of from about 3:1 to about 10:1 or more, the reaction product will be composed primarily of the dimer. As indicated above, the dimer will be formed as a mixture of the 2,2′, 2,4′ and 4,4′-diamine isomers.

Formaldehyde may be employed in any of its commercially available forms. Thus, formalin, paraformaldehyde, "stabilized" methanol solutions of formaldehyde, etc., may be employed.

The reaction may be conducted in the presence or absence of a solvent. When a solvent is to be employed, it may be any of the conventionally known hydrocarbon solvents or chlorinated hydrocarbons, such as aromatic or aliphatic solvents boiling within the range from about 100° to about 200° C. The solvent should be employed in an amount sufficient to provide a single phase solution of the amine compound.

The reaction conditions to be employed may suitably include a reaction temperature within the range of about 75° to about 150° C., and more preferably within the range of about 90° to about 105° C.

Pressure is not particularly critical with respect to the process. However, the pressure should be sufficient to provide for liquid phase reaction conditions. Thus, pressures ranging from atmospheric up to 1000 psig may be employed.

The reaction proceeds smoothly under the above described conditions, and is normally substantially complete upon heating for 1–3 hours at 90°–105° C., after the formalin addition is completed. However, because of the exothermic nature of the reaction, it is normally preferable to add the formaldehyde at a rate such that a temperature of 20°–70° can be maintained. It is desirable to have a temperature of about 65°–70° C. in the reacting mass at the completion of formalin addition. The reaction mass is then heated to 90°–105° C. and held at this temperature (with stirring) for 1–3 hours.

The polyaminopolyphenylmethanes of the present invention are recovered from the reaction mixture by extracting the catalyst salts. The reactor crude is contacted with aniline and water in a batch or continuous extractor. The organic phase, after sufficient extraction/aniline exchange will consist of aniline and diaminodiphenylmethane isomers and polyamines and the aqueous phase will consist of the aniline and polyamine salts of the hydroxy ethane sulfonic acid catalyst used in the reaction. Evaporation of water from the aqueous phase produces a concentrated catalyst salt suitable for use in further condensations (recycle catalyst). The organic phase after sufficient treatment (extraction with water and aniline) can be stripped readily of aniline leaving a polymeric amine with diamino diphenyl methane isomers. If it is desired to separate the diamine from the polyamine the diamine is flashed from the nonvolatile polyamine residue. The overhead product may be removed, for example, at from about 170° C. to about 200° C. and at about 0.5 to about 0.025 mm Hg pressure and will consist essentially of diaminodiphenylmethane.

The dimer and higher products of the present invention are useful for a variety of purposes. For example, they may be utilized as raw materials for the production of the corresponding polyisocyanates, or used as such as epoxy curing agents.

There are many and surprising advantages associated with the use of hydroxy ethane sulfonic acid compared to other known catalysts and particularly methane sulfonic acid and hydrochloric acid. For example, it has been found that the salts of hydroxyethane sulfonic acid (HESA) are much more soluble than the corresponding aniline salt of methane sulfonic acid (MSA) leading, of course, to less solids build-up. In addition, during reaction heat-up, after all the formaldehyde has been added, the physical state of the reaction mass is better with HESA catalyst than with MSA, with fewer solids being present. Also, it has been noted that one may extract HESA with water more efficiently compared to like extraction of MSA. Lastly, the physical state of the recycle catalyst in the case of HESA is better than with MSA in that the former is usually a liquid at room temperature while the latter tends to solidify and therefore be much more difficult to handle as feed into the reactor for the next run.

The following examples illustrate the process of the invention. It is understood, of course, that these examples are merely illustrative, and that the invention is not to be limited thereto.

EXAMPLE I

Aniline (256 ml, 2.7 moles) was added to a cylindrical double-walled stirred reactor. To the aniline was added a 2-hydroxyethanesulfonic acid (HESA) solution containing 750 meq. HESA (added 143.8 g of HESA solution containing 5.215 meq/g or 135 g of 70% HESA+8.8 g of $H_2O$ or 94.5 g pure HESA (0.75 mole) and 48.3 g water). At 18° C. there were no solids. It should be noted here that if methane sulfonic acid (MSA) or HCl were used and the level of water concentration approximately similar, then solids would have been expected in the initial catalyst salt formation step. Formalin addition was started at a reactor temperature of 18°–19° C. (turbine stirred) and continued for 14 minutes until complete (added 113 ml formaldehyde or 1.5 moles). The temperature rose to 64° C. during the addition and well dispersed, finely divided solids formed after about ⅔ of the formalin was added. The solids during the final portion of formalin addition and during subsequent heat-up to 80° C. were more easily handled than when MSA or HCl catalyst used. The reaction mixture was held at 80° C. for 1 hour and thereafter the solids were essentially gone—only a few traces remained. The reaction mixture was heated further (with slow $N_2$ purge) to 95°–96° C. and held there for 2.0 hours. To the reactor effluent was added $H_2O$ in 50 ml portions till turbidity was observed (300 ml $H_2O$ needed) at ~28°–30° C. and allowed to stand overnight to separate layers. 592 meq acidity was found in the aqueous layer and 149 meq in the organic layer. Treatment of the organic layer with water and aniline further reduced the acidity to about 10.8 meq of total acid out of 750 meq starting. At this point the organic layer was "polish neutralized"[1] and water and aniline removed leaving the amine product. The product contained 9.90 meq/g total amine content and 0.058 meq/g tertiary amine content. The product amine was completely soluble in chlorbenzene at the 6% level at 65°–70° C. and contained some 37.6% MDA (methylene dianiline) by GLC (wt%). GLC data further indicated the dimer portion of the polyamine consisted of only a trace of 2,2′-isomer, 5.7% 2,4′-isomer, and 94.3% 4,4′-isomer. GPC data (A%) indicated a product distribution consisting of 35% dimer, 27% trimer, and 38% heavies. THE NMR indicated a substantially complete reaction, and absence of N-benzylic type protons. In several experiments comparative extractive data showed HESA was extractable to a greater degree than either MSA or HCl. Further, upon concentration, the recycle HESA catalyst frequently remained liquid while the MSA recycle catalyst at the same concentration would solidify.

(1) After neutralization, 3–4 water washes were employed to make sure there was no salt in the amine product.

EXAMPLE II

Here the procedure of Example I was followed except that 402 g (4.32 moles) of aniline were mixed with 203.4 g of a 74.4% HESA solution (25.6% $H_2O$) that contained 5.902 meq/g acidity or 1,200 meq total acidity, followed by the addition of 180 ml (2.4 moles) of formalin. The product was worked up by neutralization and contained some 9.82 meq/g total amine content and 0.05 meq/g tertiary amine content. The reaction physical state was excellent during formalin addition after addition was complete and during heat-up. The GPC (A%) indicated 49% dimer, 25% trimer and 26% heavies. GLC indicated 51.0 wt% MDA and 95.4% 4,4'-isomer content in the dimer portion.

EXAMPLE III

In a similar procedure to Example I, the aniline/formaldehyde mole ratio was 1.9/1 and 62.5 mole% HESA basis formaldehyde was used. Also 56 ml additional $H_2O$ (over and above the amount for a 70% HESA solution) per mole HESA was used. The formalin was added at 34°–58° C. over a 25 minute period. The reaction mixture was heated to 80° C. and held for 1 hour and then heated to 95°–97° C. for 3.0 hours. The neutralized product amine was water washed and stripped and found to contain 9.97 meq/g total amine content and 0.03 meq/g tertiary amine content. The product amine was soluble in chlorobenzene at the 6% level at 55°–60° C. GPC (A%) indicated 56% dimer, 25% trimer and 19% heavies. GLC indicated 56.7 wt% MDA and 96.4% 4,4'-isomer content in the dimer portion. The NMR indicated no unrearranged N-benzylic protons and only 0.6 Rel A% $N-CH_3$ type protons.

EXAMPLE IV

Here the amine of Example I was phosgenated to produce a high quality polymeric isocayate.

EXAMPLE V

Here several runs were made using hydrochloric acid catalyst and a methane sulfonic acid catalyst as compared to the catalyst of the invention, hydroxy ethane sulfonic acid. The following observations were noted in running the side-by-side comparison.

In the early part of the aniline-formaldehyde reaction (that is at about two-thirds of the formaldehyde added to the aniline and catalyst) at 50°–70° C. that solids were much finer and softer, i.e., easier to handled in employing hydroxy ethane sulfonic acid versus use of either the hydrochloric acid or methane sulfonic acid. Even when hydroxy propyl sulfonic acid was employed, it was noted that the physical state of the reaction mass was better with the hydroxy ethane sulfonic acid catalyst.

After the reaction was completed extraction with water was effected to recover catalyst as the aniline or MDA salt. When hydroxy ethane sulfonic acid was employed said extraction could be carried out much more efficiently than when methane sulfonic acid or hydrochloric acid catalyst was used. That is, with a given amount of water one could extract more of the catalyst or to extract the catalyst completely required fewer water washes with hydroxy ethane sulfonic acid versus methane sulfonic acid or hydrochloric acid.

Lastly, upon concentration of the recovered hydroxy ethane sulfonic acid catalyst used as recycled catalyst such material was much more soluble and tended to solidify to a much lesser degree than with respect to methane sulfonic acid or hydrochloric acid salts.

We claim:

1. A method of preparing diaminodiphenylmethane and higher homologues thereof which comprises the step of condensing aniline and formaldehyde in the presence of a hydroxy ethane sulfonic acid catalyst and recovering said catalyst by extraction of the salt thereof with water.

2. The method of claim 1 wherein said catalyst is present in an amount ranging from about 10 to about 70 mole percent based on the moles of aniline present.

3. The method of claim 2 wherein said catalyst is present in an amount of 20–40 mole percent basis moles of aniline.

* * * * *